United States Patent [19]

Yoshida

[11] Patent Number: 4,682,023

[45] Date of Patent: Jul. 21, 1987

[54] BOTTLE SIDEWALL DEFECT DETECTOR EMPLOYING MASKING MEANS

[75] Inventor: Hajime Yoshida, Tokyo, Japan

[73] Assignee: Hajime Industries Ltd., Tokyo, Japan

[21] Appl. No.: 834,639

[22] Filed: Feb. 28, 1986

[30] Foreign Application Priority Data

Mar. 12, 1985 [JP] Japan .................................. 60-48689

[51] Int. Cl.⁴ ............................................. G01N 9/04
[52] U.S. Cl. .................................. 250/223 B; 356/240
[58] Field of Search .................... 250/223 B; 356/240; 209/526

[56] References Cited

U.S. PATENT DOCUMENTS 3,133,640  5/1964  Calhoun et al. ................. 250/223 B
3,328,000  6/1967  Rottmann ........................ 250/223 B
3,500,053  3/1970  Calhoun ........................... 250/223 B
4,435,641  3/1984  Hajime ............................. 250/223 B Primary Examiner—David C. Nelms
Assistant Examiner—Chung Seo
Attorney, Agent, or Firm—Murray Schaffer

[57] ABSTRACT

A defect inspection apparatus for bottles made of transparent material in which a light source is located under a bottle made of transparent material and to be inspected for irradiating a bottom of the bottle, a photoelectric conversion sensor is installed above the mouth of the bottle for receiving such a light that enters the bottle from its bottom, passes through the inside of the sidewall of the bottle and then is emitted upwards from the mouth of the bottle and, an electric processor is provided for electrically processing the responsive electrical signal from the photoelectric conversion sensor to thereby inspect defects of the bottle.

4 Claims, 9 Drawing Figures

BOTTLE SIDEWALL DEFECT DETECTOR EMPLOYING MASKING MEANS

BACKGROUND OF THE INVENTION

1. Field of the Invention

The present invention relates generally to defect inspection apparatus for bottles made of such transparent material as glass bottles, for example, and is especially related to bottle defect inspection apparatus that use such photoelectric conversion sensor like television cameras.

2. Description of the Prior Art

Those dealers that are engaged in handling glass bottles which are used to preserve and sell spirits, beverages or liquids or the like, are necessitated with sufficient cautions in handling such bottles. Especially, as for the bottle mouth conditions, if there are breakage, chips, cracks or defects or the like, at the ossasions of filling the fluid and/or capping the bottle, various trouble will occur due to incomplete capping, whereas the content liquid will leakout during transportation of the bottles, or it could be dangerous when the bottle mouth contacts the human mouth or lip. Especially when recycled or refilling type bottles are recollected for reuse, during the circulation of these bottles, the bottles often are damaged especially at the mouth portion so that, attention must be provided to whether the bottle mouth portion has a defect or not.

Therefore, at fluid production plants such as breweries or the like, prior to filling the bottle with liquid after washing the bottles, for example, it was customary that visual inspectors that depend upon their visual sights, checked the damages at the bottle mouth portion and removed the ones that were judged as a defective bottle.

It was through the recent years that in order to replace the human inspection, the bottle defects, especially the mouth portion defects thereof are detected photoelectrically by photoelectric conversion means such as photoelectric sensors and defective bottles were automatically rejected came into practical use.

The conventional methods that are used to detect bottle mouth defects photoelectrically are such that light is irradiated onto the bottle mouth from the top or side thereof, the reflection light thereon is picked up to be converted into electrical signals by such photoelectric conversion sensor means like a photosensors or video cameras that are placed on the top or at the side of the bottle mouth, and such electrical signal is processed by an electronic processor such as a computor as an example, to electrically judge whether or not there is a defect or abnormality at the bottle mouth.

However, as shown on FIG. 1, there were such defects as F at a mouth portion $2c$ of a bottle 2 as one example, that are cracks on a very smooth surface (not complexed) or those that are vertical thin crack lines that go down from the bottle mouth $2c$ as shown on FIG. 2, or otherwise are hidden by an upper edge portion $2c_1$, that sticks out at the bottle mouth $2c$ as shown on FIG. 3, whereas the reflection light from the defects F do not reach the defect detection section such as photoelectric sensors that are placed above the top of the mouth portion $2c$, so that the conventional apparatus that depend upon the reflected light from the defects, carry the fault that such defect detection was difficult.

Next, with reference to FIG. 4, one example of such above mentioned conventional bottle mouth defect detection device will be explained. In FIG. 4, 1 is a photoelectric conversion sensor such as a television camera or the like, which is placed above the top of bottle mouth $2c$ of the bottle 2 to be inspected. 3 is an electronic processor which electrically processes the electrical signals from the television camera 1, 4 is a circular light source that is placed above the top of the inspected bottle 2, but is under the television camera 1.

According to this conventional example, by the light source 4 such as a fluorescent circuline as an example, the bottle mouth $2c$ of the bottle 2 is irradiated whereas such reflection light therefrom is picked up by the television camera 1, which is converted into electrical signals which are processed by the electronic processor 3, to thereby detect the existence or not of defects around the bottle mouth portion $2c$ of the bottle 2.

According to the conventional bottle mouth flaw inspection devices as said hereabove, when the defect F at the mouth portion $2c$ of the bottle 2 to be inspected is very smooth surfaced, or is a thin lined vertical crack that goes down from the bottle mouth $2c$ of the bottle 2, or when it is located inside and under the bottle mouth top outer edge $2c_1$ of bottle mouth $2c$ of bottle 2, although the light from light source 4 that is placed above the bottle mouth $2c$ of bottle 2, arrives at the bottle mouth $2c$ of bottle 2 and reflects on defect F, such reflection light will not reach the photoelectric conversion sensor 1 such as the television camera, and accordingly the detection of the defects was impossible.

OBJECTS AND SUMMARY OF THE INVENTION

It is an object of the present invention to provide an improved defect inspection apparatus for a bottle made of transparent material.

It is a further object of the present invention to provide a defect inspection apparatus for a bottle made of transparent material in which a photoelectric conversion sensor is employed.

It is a yet further of object of the present invention to provide a defect inspection apparatus for inspecting a defect on the mouth of a bottle made of transparatus material.

According to an aspect of the present invention, there is provided a defect inspection apparatus for bottles made of transparent material comprising:

a light source located under a bottle made of transparent material and to be inspected for irradiating a bottom of said bottle;

a photoelectric conversion sensor installed above a mouth of said bottle for receiving such a light that enters said bottle from its bottom, passes through the inside of the sidewall of said bottle and then is emitted upwards from the said mouth and; an electric processer for electrically processing a responsive electrical signal from said photoelectric conversion sensor to thereby inspect defects of said bottle.

These and other objects, features and advantages of the present invention will become apparent from the following detailed description of the preferred embodiment taken in conjunction with the accompanying drawings, throughout which like reference numerals designate like elements and parts.

DESCRIPTION OF THE PREFERRED EMBODIMENTS

Figure 4:
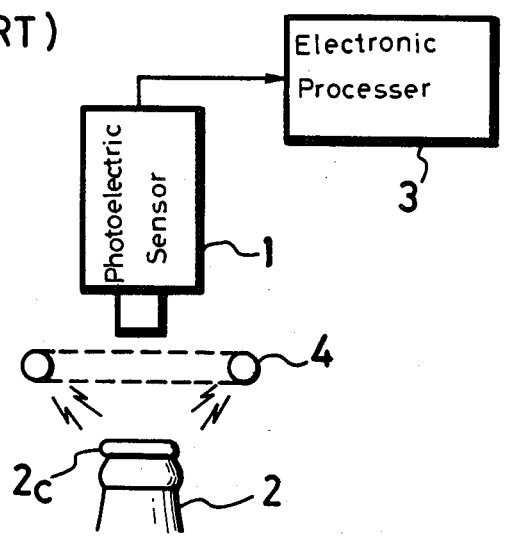
FIG. 4 is diagram showing an outline of a conventional device.

The present invention will be explained hereunder in reference with the attached drawings. First, one example of the present invention will be explained in reference with FIG. 5 which illustrates such outlines. Further, the like references on FIG. 5 and FIG. 4 designate the same elements. In the example of the present invention as shown on FIG. 5, it equally uses like in the example of the conventional art as shown on FIG. 4, a photoelectric conversion sensor 1 such as a television camera, which is placed above the bottle mouth 2c of the inspected bottle 2 made of transparent material such as glass or the like, and the output electrical signal therefrom is processed by an electronic processer 3.

In this example of the present invention, a normal light source 5 is placed under a bottom 2a of bottle 2 to irradiate the bottom 2a of the bottle 2. In this case, if necessary, a mask plate 6 which has an opening 6a so as to effectively irradiate the bottom 2a is placed between the bottom 2a and light source 5 so that the light may be confined such that the light from the light source 5 enter only the bottle bottom 2a. The light that enters inside the bottle 2 from the bottom 2a travels through a transparent sidewall 2b of the bottle 2 and is emitted upwards from the bottle mouth 2c. If it is preferable that the photoelectric sensor 1 such as a television camera picks up only the light emitted from the bottle mouth 2c to avail good precisioned defect inspection, an optical mask 7 is located between the television camera 1 and the bottle mouth 2c which has a light transmission portion of a ring shape which generally responds to the shape of the bottle mouth 2c so that any other unnecessary lights than that as emitted from the bottle mouth 2c (especially the light that passes through the bottle bottom 2a and comes up straight) are prevented from entering the television camera 1. Further, if the optical axis of the television camera 1 and the center axis of the bottle 2 are matched and then the light source 5 is placed on such extension line, it will be better suitable for the above purpose.

Figure 3:
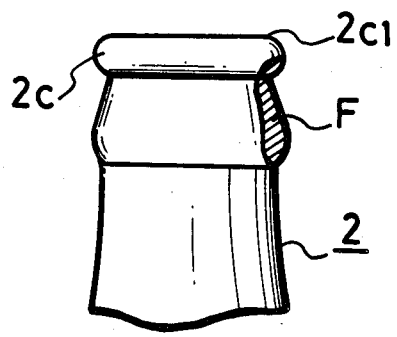
Figure 6A:
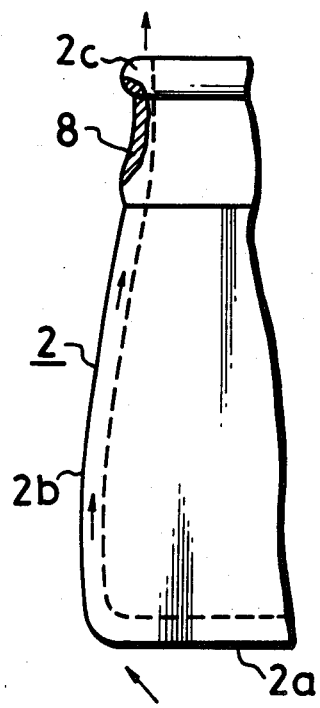
FIGS. 6A, 6B and 6C are schematic diagrams used for the explanation of the present invention, respectively.
Figure 6B:
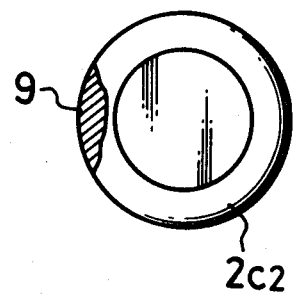

Next, further details of the functions of the present invention will be explained in reference with FIG. 6. As shown on FIG. 6A, the light that enters the bottle 2 from its bottom 2a, takes the passage as shown by the arrows through its sidewall 2b to pass upwards from bottle mouth 2c. At such instance, if there is a defect on the side of the bottle mouth 2c as referenced as 8 (This corresponds to the defect F as shown on FIG. 3), the intensity of the light passing therethrough is reduced. Therefore, when such light is optically observed above the top of the bottle mouth 2c, as shown on FIG. 6B, amongst a ring shape light portion 2c₂, a dark shade that responds to defect 8 as shown by hatched lines 9 will appear. Therefore, when such responsive electrical signal from the photoelectric sensor 1 that receives this light is electrically processed by a simple construction of electronic processer 3 such as a micro computor, for instance, when such electrical signal from the photoelectric sensor in response to a bottle without a defect is compared with the electrical signal responsive to a defect bottle, even though not visible from the top side, in other words, such defects 8 that could not be detected by devices of conventional methods, can be detected by the present invention.

Figure 6C:
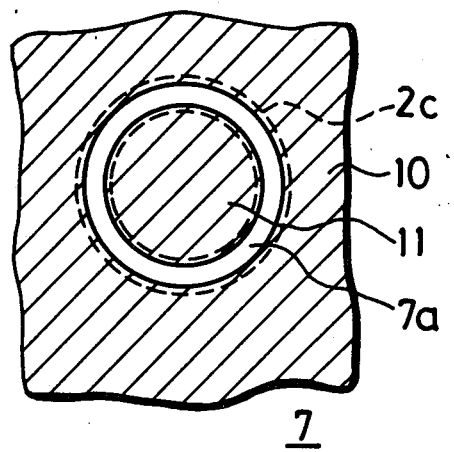

FIG. 6C illustrates a top view of optical mask 7. As shown on FIG. 6C, this optical mask 7 is provided with the above-mentioned light transmission portion 7a which is defined by an opaque outer mask 10 which has a disc-shaped transparent portion the outer diameter of which is somewhat smaller than the outer diameter of the upper surface of bottle mouth 2c as indicated by the broken line and a disc-shaped opaque inner mask 11 that has an outer diameter that is somewhat larger than the inner diameter of the upper surface of bottle mouth 2c as indicated by the broken line. Accordingly, the photoelectric sensor 1 can photosense only the light emitted from the necessary portion of the top surface of bottle mouth 2c.

In this example, the occasion that the physical optical mask 7 was provided outside the photoelectric sensor 1 to shield the light from the unnecessary portions for the photoelectric sensor 1 was explained, but it may be possible that, for instance, within the electronic circuitry of electric processer 3 or the like, an electronic masking which will carry out the masking function same as that of this physical mask 7 is provided and only the necessary portions of the electrical signal are processed electrically by such electronic masking to omit this physical mask 7.

Figure 1:
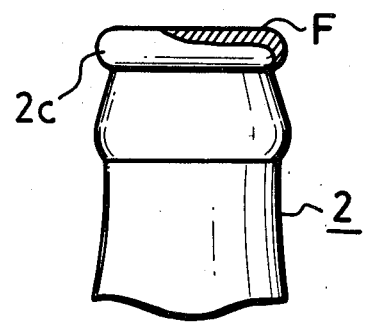
FIGS. 1 to 3 are schematic drawings used to explain the type of defects on bottles that are detected by the present invention.
Figure 2:
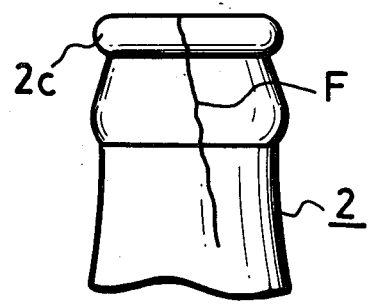

Further, it is obvious without need of explanation that such defects as F as shown on FIGS. 1 and 2, and further, such defects on the side wall 2b of bottle 2, can be well detected by the present invention.

Figure 5:
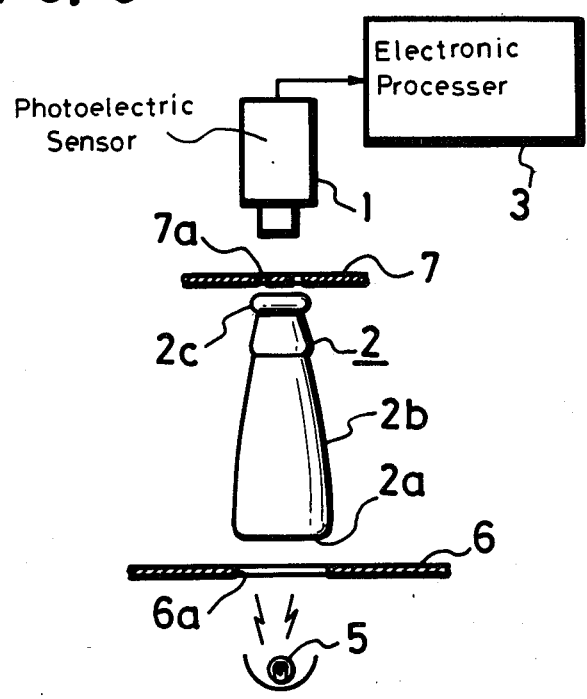
FIG. 5 is a schematic diagram illustrating an outline of one example of the present invention.
Figure 7:
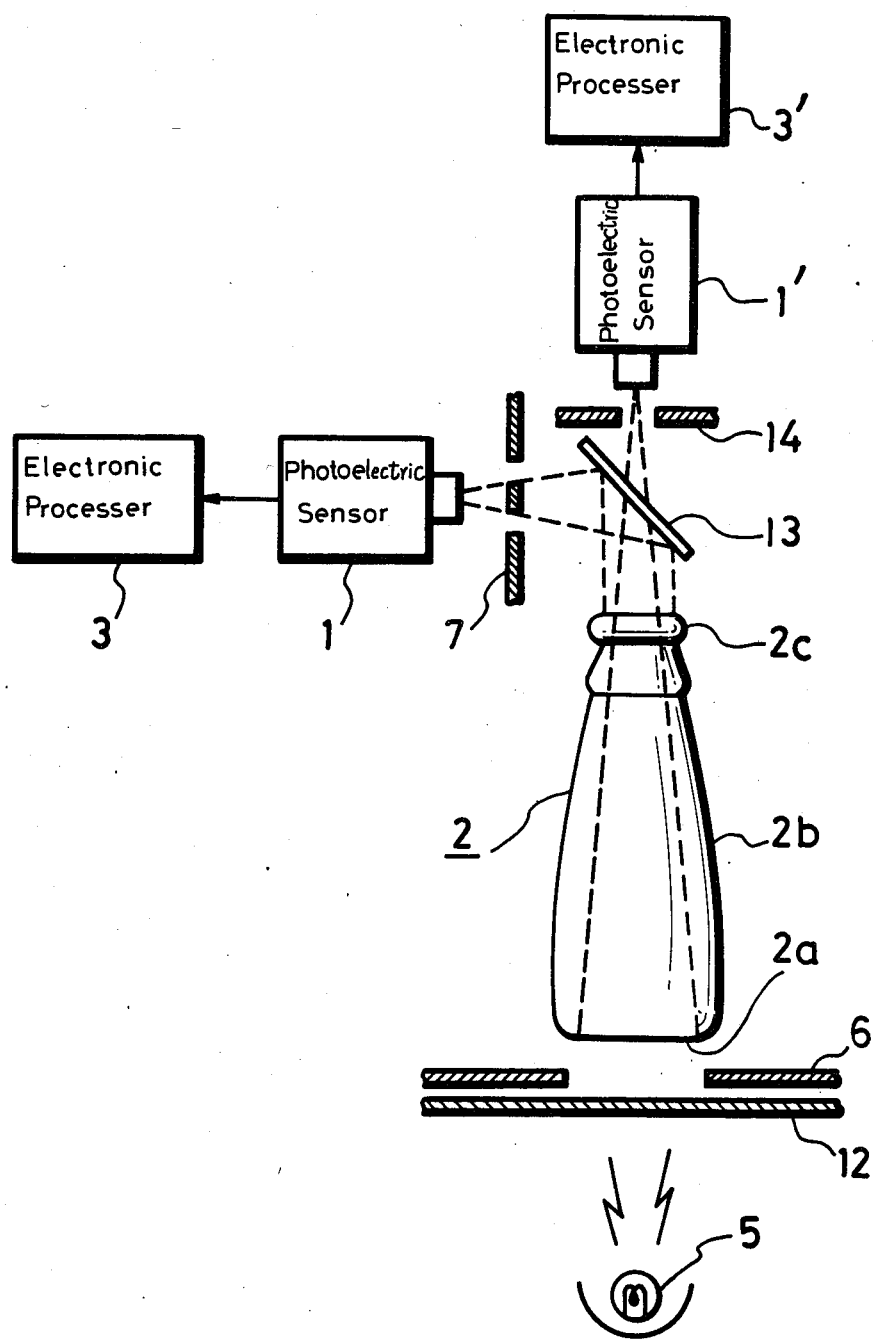
FIG. 7 is a schematic diagram showing another example of the present invention.

FIG. 7 illustrates another example of the present invention. In this case, the example of the present invention as shown on FIG. 5 is applied and installed together with a prior art bottle bottom inspection device which detects the bottle bottom defects and foreign particle mixtures thereon by lighting from under the bottle bottom. In other words, to the prior art bottle bottom inspection device in which the bottle bottom 2a is irradiated upon through the diffuser screen 12 by light source 5 located under the bottle bottom 2a, the light that passes bottle bottom 2a is viewed by the photoelectric sensor 1' that is placed above the top of bottle mouth 2c and the bottle bottom 2a is inspected, there is applied the defect inspection apparatus of the present invention in such a manner that a half mirror 13 is placed between the photoelectric sensor 1' and the bottle mouth 2c and the reflected light thereon is introduced through the optical mask 7 of the present invention into photoelectric sensor 1 to thereby inspect the defects of bottle mouth 2c as above described. Further, in FIG. 7, 14 is a mask that is used to enable such above mentioned photoelectric sensor 1' of the conventional device photosenses only the bottle bottom 2a.

By such arrangement as shown on FIG. 7, by using a single light source 5, both of the bottle mouth 2c and the bottle bottom 2a can be simultaneously inspected.

Further, on FIG. 7, 6 indicates the above described mask plate of the present invention and 3' is an electronic processor for the conventional device that is similar to the electronic processer 3 of the present invention.

In addition, without escaping the scope of the novel concepts of the present invention, it is apparent that any concern skilled in the art may conduct many variations and changes, so that the scope of the invention should be determined by the appended claims only.

I claim as my invention:

1. A defect inspection apparatus for bottles made of transparent meterial comprising:

a light source located under a bottle made of transparent material and to be inspected for irradiating a bottom of said bottle;

a photoelectric conversion sensor installed above a mouth of said bottle for receiving such a light that enters said bottle from its bottom, passes through the inside of the sidewall of said bottle and then is emitted upwards from the said mouth and;

an electric processer for electrically processing a responsive electrical signal from said photoelectric conversion sensor to thereby inspect defects of said bottle.

2. A defect inspection apparatus according to claim 1 further comprising an optical mask located between said mouth of the bottle and said photoelectric conversion sensor, said optical mask having a transparent portion a shape of which corresponds to a shape of the mouth of said bottle.

3. A defect inspection apparatus as claimed in claim 2, in which the transparent portion of said optical mask is of a ring-shape whose outer diameter is smaller than an outer diameter of the mouth of said bottle and whose inner diameter is larger than an inner diameter of said mouth.

4. A defect inspection apparatus according to claim 1 further comprising an optical mask between said light source and the bottom of said bottle, said optical mask having an opening so as to make a light from said light source incident only on the bottom of said bottle.

* * * * *